(12) United States Patent
Gadladge (10) Patent No.: US 9,119,614 B2
(45) Date of Patent: Sep. 1, 2015

(54) SUTURE RETENTION DEVICE

(71) Applicant: Kristyn G. Gadladge, Beech Grove, IN (US)

(72) Inventor: Kristyn G. Gadladge, Beech Grove, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 187 days.

(21) Appl. No.: 13/766,084

(22) Filed: Feb. 13, 2013

(65) Prior Publication Data

US 2013/0218206 A1    Aug. 22, 2013

Related U.S. Application Data (60) Provisional application No. 61/599,687, filed on Feb. 16, 2012.

(51) Int. Cl.
- *A61B 17/04* (2006.01)
- *A61B 17/06* (2006.01)
- *A61B 17/11* (2006.01)

(52) U.S. Cl.
CPC ......... *A61B 17/0401* (2013.01); *A61B 17/0487* (2013.01); *A61B 2017/0417* (2013.01); *A61B 2017/0496* (2013.01)

(58) Field of Classification Search
CPC ........... A61B 17/0401; A61B 17/0487; A61B 17/0483; A61B 17/0466; A61B 17/06004; A61B 17/06061; A61B 17/08; A61B 17/083; A61B 17/11; A61B 17/1146; A61B 17/1227; A61B 2017/0417; A61B 2017/0496; A61B 2017/0403; A61B 2017/0404; A61B 2017/0406; A61B 2017/0408; A61B 2017/0414; A61B 2017/0419; A61B 2017/0438; A61B 2017/0446; A61B 2017/0448; A61B 2017/045; A61B 2017/0451; A61B 2017/0454; A61B 2017/0458; A61B 2017/0461; A61B 2017/0462; A61B 2017/06009; A61B 2017/06014; A61B 2017/06019; A61B 2017/06023; A61B 2017/088; A61B 2017/1142; A61B 2/0811; A61B 2002/0817; A61B 17/044
USPC ......... 606/232, 148, 228, 233, 213, 144, 147, 606/139; 604/174, 175, 178; 24/115 G, 24/136 R, 115 H, 136 K
See application file for complete search history.

(56) References Cited

U.S. PATENT DOCUMENTS

| | | | |
|---|---|---|---|
| 4,328,605 A | | 5/1982 | Hutchison et al. |
| 4,506,417 A | | 3/1985 | Hara |
| 5,323,514 A | | 6/1994 | Masuda et al. |
| 5,361,461 A | | 11/1994 | Anscher |
| 5,364,407 A | | 11/1994 | Poll |
| 5,379,496 A | | 1/1995 | Krauss |
| 5,514,159 A | | 5/1996 | Matula et al. |
| 5,531,763 A | * | 7/1996 | Mastri et al. ............ 606/148 |
| 5,671,505 A | | 9/1997 | Anscher |
| 5,725,539 A | | 3/1998 | Matern |
| 5,911,728 A | | 6/1999 | Sepetka et al. |
| 6,018,851 A | | 2/2000 | Anscher |

(Continued)

*Primary Examiner* — Katrina Stransky
*Assistant Examiner* — Katherine Schwiker
(74) *Attorney, Agent, or Firm* — Brinks Gilson & Lione (57) ABSTRACT

A suture retention device is provided for retaining a suture. The device has a locked state and an unlocked state. In the locked state, a spring biases a first gripping surface and second gripping surface together to enmesh a suture to prevent the suture from sliding through the device. In the unlocked state, an actuator may be engaged to bias the spring and separate the first and second gripping surfaces to allow the suture to freely slide through the device.

20 Claims, 5 Drawing Sheets

(56) References Cited

U.S. PATENT DOCUMENTS

| | | |
|---|---|---|
| 6,126,677 A | 10/2000 | Ganaja et al. |
| 6,293,961 B2 | 9/2001 | Schwartz et al. |
| 6,457,214 B1 * | 10/2002 | Boden .................. 24/136 R |
| 6,475,230 B1 | 11/2002 | Bonutti et al. |
| 6,488,501 B1 * | 12/2002 | Harding .................. 433/173 |
| 6,648,903 B1 | 11/2003 | Pierson, III |
| 7,094,251 B2 | 8/2006 | Bonutti et al. |
| 7,270,671 B2 | 9/2007 | Fuseri et al. |
| 7,785,348 B2 | 8/2010 | Kuhns et al. |
| 7,867,253 B2 | 1/2011 | McMichael et al. |
| 7,875,056 B2 * | 1/2011 | Jervis et al. .................. 606/232 |
| 2002/0133920 A1 * | 9/2002 | Hodge .................. 24/590.1 |
| 2006/0004409 A1 | 1/2006 | Nobis et al. |
| 2006/0004410 A1 | 1/2006 | Nobis et al. |
| 2007/0276437 A1 | 11/2007 | Call et al. |
| 2007/0294807 A1 * | 12/2007 | Van Cotthem .................. 2/321 |
| 2009/0222083 A1 * | 9/2009 | Nguyen et al. .................. 623/2.11 |
| 2010/0057110 A1 * | 3/2010 | Lampropoulos et al. ..... 606/148 |
| 2010/0292733 A1 * | 11/2010 | Hendricksen et al. ........ 606/232 |
| 2010/0305609 A1 | 12/2010 | Cartledge et al. |
| 2011/0106155 A1 | 5/2011 | Theobald et al. |

* cited by examiner

SUTURE RETENTION DEVICE

This application claims priority to U.S. Provisional Application No. 61/599,687, filed Feb. 16, 2012, which is hereby incorporated by reference herein.

BACKGROUND

The present invention relates generally to medical devices and more particularly to a device to retain a suture.

Suture retention devices are sometimes used in percutaneous direct feeding methods to secure a tethering suture to the exterior of a patient. In such methods, a gastrostomy or gastrojejunostomy tube is inserted through a patient's abdominal wall and stomach or jejunum wall to provide nutrients directly to the gastrointestinal tract. A wide range of medical diseases and conditions may require a patient to be fed by this type of feeding method, such as esophageal cancer, anorexia, Chrome's disease, and neurodegenerative disorders, such as multiple sclerosis.

In order to maintain the wall of the stomach or jejunum in the proper location for feeding through the gastrostomy or gastrojejunostomy tube, anchors may be placed against the interior wall of the stomach or jejunum. Tethering sutures attached to the anchors may pass through the wall of the stomach or jejunum and the abdominal wall, and the loose ends of the sutures may be secured against the exterior of the patient's abdominal wall either by directly suturing the tethering suture to the patient's tissue or with various types of suture retention devices. As a result, the stomach or jejunum can be pulled against the interior surface of the abdominal wall so that the depth of the stomach or jejunum is precisely located. The lateral position of the stomach or jejunum is also controlled since the stomach or jejunum is prevented from moving relative to the abdominal wall.

Although suture retention devices are particularly useful in direct feeding medical procedures, suture retention devices may also be used in other medical procedures as well.

SUMMARY

A suture retention device is described. The device has a housing with an inner cavity and a sliding body within the inner cavity. A spring biases the sliding body toward one side of the inner cavity to enmesh a first and second gripping surface. A suture hole extends through the housing and is located so that a suture extending through the suture hole is enmeshed with the first and second gripping surfaces in a locked state. An actuator may be used to separate the first and second gripping surfaces to unlock the device and allow the suture to freely slide through the suture hole. The inventions herein may also include any other aspect described below in the written description, the claims, or in the attached drawings and any combinations thereof.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
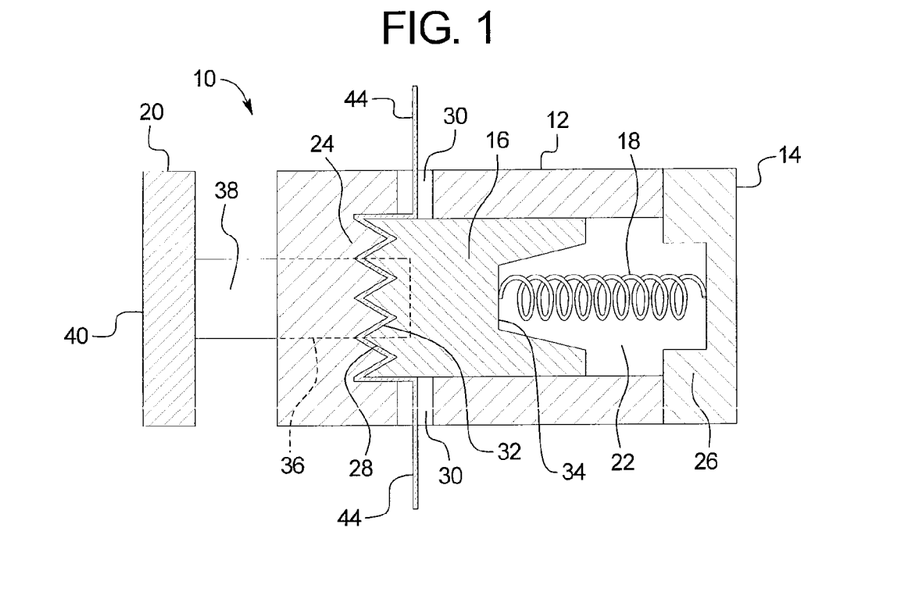
FIG. 1 is a cross-sectional view of a suture retention device in a locked state.
Figure 2:
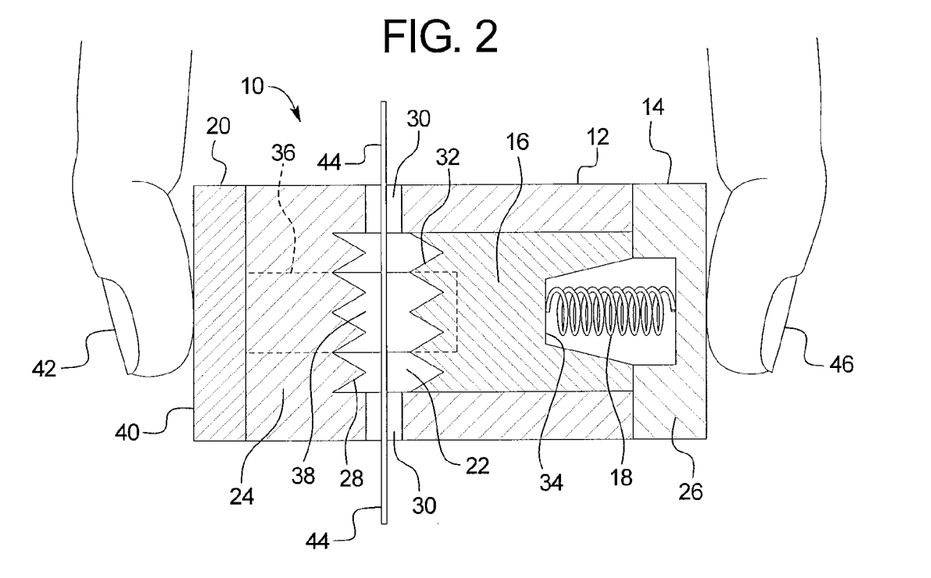
FIG. 2 is a cross-sectional view of the suture retention device in an unlocked state.

Referring now to the figures, and particularly to FIGS. 1 and 2, a suture retention device 10 is shown. Preferably, the suture retention device 10 includes a first housing 12, a second housing 14, a sliding body 16, a spring 18, and an actuator 20. The first and second housings 12, 14 define an inner cavity 22 with a first side 24 and a second side 26. Preferably, the first housing 12 defines the first side 24, and the second housing 14 defines the second side 26, with the first and second side 24, 26 being opposite from each other. The first side 24 of the inner cavity 22 is provided with a first gripping surface 28, which may be a series of teeth 28. The first housing 12 is also provided with a suture hole 30 that extends laterally through the walls of the first housing 12. The suture hole 30 may be positioned along the first housing 12 so that the suture hole 30 passes through the inner cavity 22 adjacent the first gripping surface 28.

The sliding body 16 is located within the inner cavity 22 and is sized to slide longitudinally within the inner cavity 22. The sliding body 16 is provided with a second gripping surface 32 that is designed to enmesh with the first gripping surface 28. Thus, where the first gripping surface 28 is a series of teeth 28, the second gripping surface 32 may be a series of teeth 32 that interlock with the teeth 28 of the first housing 12. Although the teeth 28, 32 are shown in the figures with sharp, pointed tips, it is also possible for the teeth 28, 32 to have flat tips or other shaped tips, and the corresponding recesses may have flat bottoms or other matching shapes if desired. A compression spring 18 may be positioned between the sliding body 16 and the second housing 14 so that the spring 18 is compressed between the second side 26 of the inner cavity 22 and the rear surface 34 of the sliding body 16 opposite from the second gripping surface 32. Thus, the spring 18 biases the sliding body 16 toward the first side 24 of the inner cavity 22 to enmesh the first and second gripping surfaces 28, 32.

Figure 5:
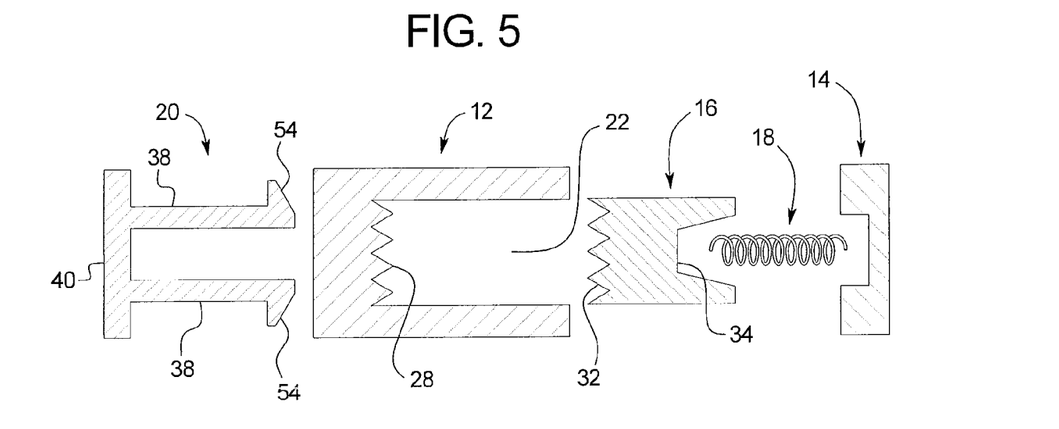
FIG. 5 is a side-exploded view of the suture retention device, showing the individual components of the suture retention device.
Figure 6:
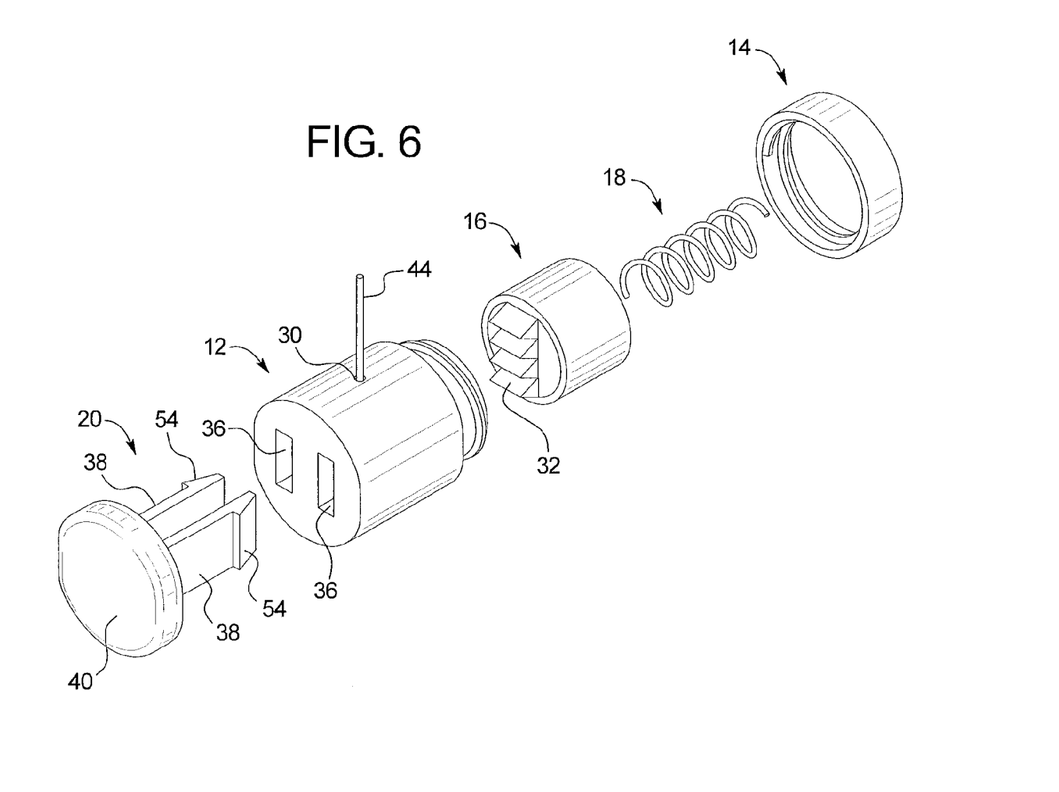
FIG. 6 is a perspective-exploded view of the suture retention device, showing the individual components of the suture retention device.

The actuator 20 extends through an opening 36 in the first housing 12 to engage the sliding body 16 and extends at least partially outside of the first housing 12. As shown in FIGS. 5-6, the portion of the actuator 20 extending through the first housing 12 may be two arms 38 that extend through two corresponding openings 36 in the first housing 12. Preferably, the arms 38 extend through the first side 24 of the inner cavity 22. The portion of the actuator 20 that extends outside of the first housing 12 includes an operator engageable surface 40 in the form of a button 40 that may be pressed by an operator's finger 42.

As shown in FIGS. 1 and 2, the suture retention device 10 may have a locked state and an unlocked state. In the locked state, shown in FIG. 1, the spring 18 biases the second gripping surface 32 of the sliding body 16 against the first gripping surface 28 of the first housing 12. As a result, a suture 44 extending through the suture hole 30 is enmeshed between the first and second gripping surfaces 28, 32, which prevents the suture 44 from being drawn through the suture hole 30. In the unlocked state, shown in FIG. 2, and operator pushes the engageable surface 40 of the actuator 24 toward the first housing 12 with one finger 42 and restrains the device 10 by placing another finger 46 on the second housing 14. As a result, the arms 38 press the sliding body 16 against the spring 18 to separate the first and second gripping surfaces 28, 32 from each other. This allows the suture 44 to freely slide through the suture hole 30 in the unlocked state. The engageable surface 40 of the actuator 20 may abut against the first housing 12 to indicate that the device 10 is unlocked.

Figure 3:
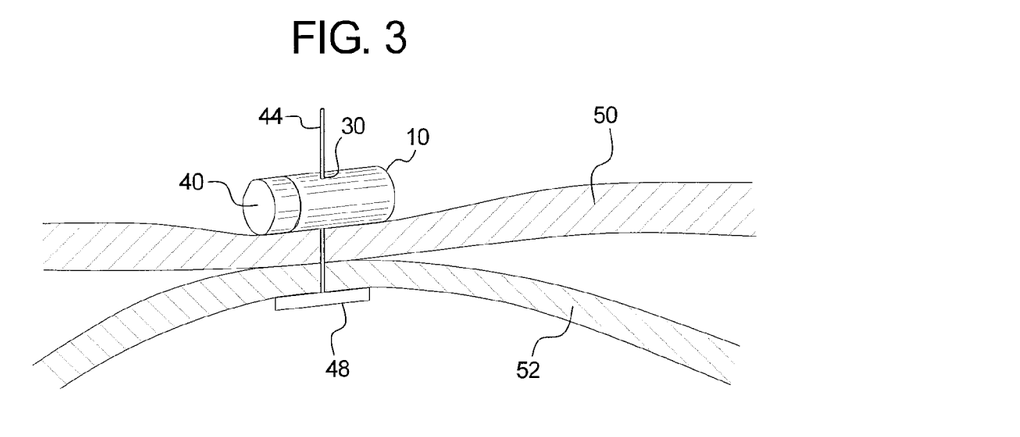
FIG. 3 is a side view of the suture retention device securing a suture against a patient's abdominal wall in a gastropexy procedure.

As shown FIG. 3, the suture retention device 10 may be used to secure a suture 44 with an anchor 48 against a patient's abdominal wall 50. For example, gastropexy is one example of how the suture retention device 10 may be used. Gastropexy procedures are typically performed by initially identifying the medial edge of the liver using CT scan or ultrasound. The stomach 52 is then insufflated with air using a nasogastric catheter until adequate distention is achieved. Using fluoroscopy, a location is chosen that allows as direct a vertical needle path as possible. A feeding tube insertion site is then determined and a gastropexy pattern is defined by placing three marks equidistant from the feeding tube insertion site in a triangular configuration. However, it is understood that a different number and different pattern could be used as desired. Approximately 2-3 cm between the insertion site and the suture anchor 48 sites is typically allowed to prevent interference between the anchors 48 and the feeding tube. A luer slip syringe containing one to three mL of sterile water is then attached to the hub of the needle. Under fluoroscopic guidance, the needle (preloaded with an anchor 48 and suture 44) is inserted with a single, sharp thrust through one of the marked corners of the triangle until it is within the gastric lumen. The simultaneous return of air into the syringe and fluoroscopic visualization confirms correct placement. The syringe is then removed from the needle and the suture 44 extends out from the hub of the needle. At this point, the anchor 48 is dislodged from the needle. This can be accomplished by inserting a wire guide through the needle, which forces the anchor 48 out, or by pushing down on the needle hub, which triggers an inner cannula to move towards the distal end of the needle, allowing the anchor 48 to be pushed out. After the anchor 48 is dislodged, the needle is withdrawn, and the anchor 48 is pulled until it is flush against the gastric mucosa 52 (stomach wall 52). At this point of the procedure, the suture 44 must be secured and locked so that the anchor 48 remains pulled tightly against the stomach wall 52. This can be accomplished through use of the suture retention device 10 described herein.

The suture retention device 10 may be provided as part of a gastrointestinal suture anchor kit for gastropexy procedures. The gastrointestinal suture anchor kit may include the anchor 48 tied to the suture 44, with the anchor 48 being housed inside the needle, and the suture 44 extending out the distal opening of the needle. As noted above, the gastropexy procedure may be used to pull the stomach wall 52 against the abdominal wall 50 prior to placing a feeding tube. Once the desired location for the suture anchor 48 has been established, the physician punctures the abdominal and stomach walls 50, 52 with the needle. While the needle extends through the abdominal and stomach walls 50, 52, the suture 44 extends from the distal opening of the needle within the stomach 52, and extends along the exterior of the needle though the stomach and abdominal walls 50, 52. Once the needle is inside the stomach 52, the physician may use a wire guide to push the anchor 48 out of the needle. During this procedure, the suture retention device 10 may rest in an out of the way location, with the suture 44 being prethreaded through the suture hole 30. When the anchor 48 is outside the needle and in the stomach 52, the needle may be removed. The suture retention device 10 may then be slid along the suture 44 to tighten the device 10 against the abdominal wall 50. Alternatively, the anchor 48 and suture 44 could be initially placed without the suture retention device 10 being threaded onto the suture 44, and the suture 44 could be threaded through the suture hole 30 after the suture anchor 48 is positioned within the stomach 52.

The physician may then unlock the suture retention device 10 by pushing the actuator 20 to allow the suture 44 to freely slide through the suture retention device 10. While the suture retention device 10 is unlocked, the physician pulls on the suture 44 to tension the suture 44 and pull the stomach wall 50 against the abdominal wall 52. While tension is maintained on the suture 44, the suture retention device 10 is slid along the suture 44 toward the abdominal wall 52 until the device 10 contacts the abdominal wall 52. Once the suture retention device 10 touches the patient's skin and the appropriate tension is reached, the physician releases the actuator 20. This causes the suture retention device 10 to lock the suture 44 in place due to the spring 18 biasing the first and second gripping surfaces 28, 32 together. If the physician desires to readjust the tension on the suture 44, the physician can push the actuator 20 again to unlock the suture retention device 10 and slide the suture 44 through the suture hole 30 to readjust the tension.

Figure 4:
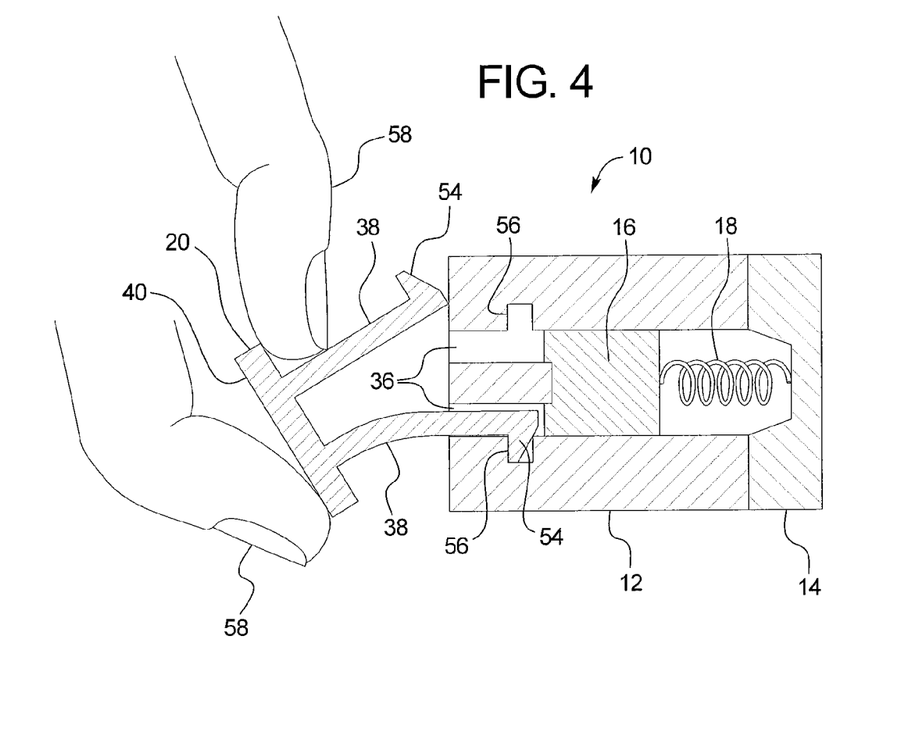
FIG. 4 is a cross-sectional view of the suture retention device, showing the actuator being removed.

As shown in FIG. 4, when the physician feels the suture retention device 10 is in its proper place and has proper tension, the physician may remove the actuator 20 to permanently lock the suture retention device 10. By providing a permanently locked state, the patient cannot accidentally move the suture retention device 10. This is important because the suture anchor 48 may be in place on the patient for up to two weeks, and accidental release of the suture anchor 48 could allow the stomach wall 50 to separate from the abdominal wall 52, which might dislodge the feeding tube or apply tension to the feeding tube. Preferably, the actuator 20 is retained on the suture retention device 10 with enough force to prevent the actuator 20 from being inadvertently removed, but is removable when the actuator 20 is intentionally pulled from the suture retention device 10. After the feeding procedure is complete, the physician could reinsert the actuator 20 into the suture retention device 10 to unlock the device 10 and free the suture 44. However, it is preferable instead to cut the suture 44 between the suture retention device 10 and the patient's skin to release the suture retention device 10. The anchor 48 and the remnant of the suture 44 may then pass through the patient's digestive tract.

In order to retain the actuator 20 on the suture retention device 10 to prevent inadvertent removal, and allow the actuator 20 to be intentionally removed, arms 38 of the actuator 20 are provided with tabs 54 that engage stop surfaces 56 on the first housing 12. Preferably, the tabs 54 and arms 38 are made from a flexible material that allows the arms 38 and tabs 54 to flex when a physician pulls on the actuator 20 with the physician's fingers 58 to free the actuator 20 from the first and second housing 12, 14. As shown in FIG. 4, the tabs 54 may be located on the arms 38 that extend into the inner cavity 22 and press against the sliding body 16. Thus, in the embodiment of FIG. 4, the stop surfaces 56 are located inside of the first housing 12. However, as further described below, the tabs 54 may be located on a different arm if so desired. Preferably, the force required to remove the actuator 20 from the suture retention device 10 is between about 1 to about 5 N. This may be accomplished by making the tab 54 and arms 38 out of a material having a Shore D durometer between about 30 to about 70. In addition, the interference between the tabs 54 and the stop surfaces 56 is preferably about 0.003" to about 0.007". Further, in order to prevent the biasing force of the spring 18 from dislodging the actuator 20, it is preferred that the sliding body 16 abut against the inner cavity 22, for example between the first and second gripping surfaces 28, 32, so that the tabs 54 are not biased against the stop surfaces 56 by the spring 18.

Figure 7:
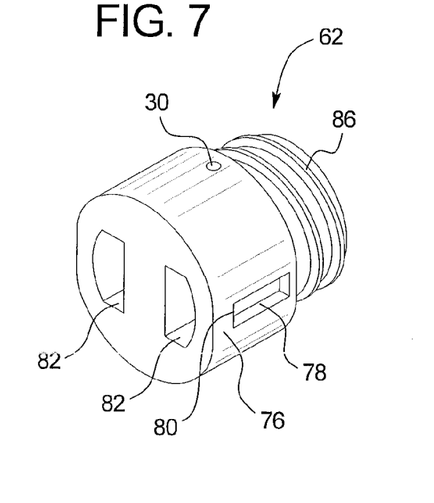
FIG. 7 is a perspective view of a first housing of another suture retention device.
Figure 8:
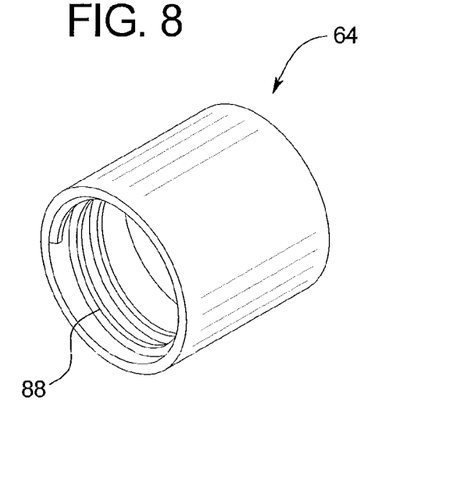
FIG. 8 is a perspective view of a second housing of the suture retention device.
Figure 9:
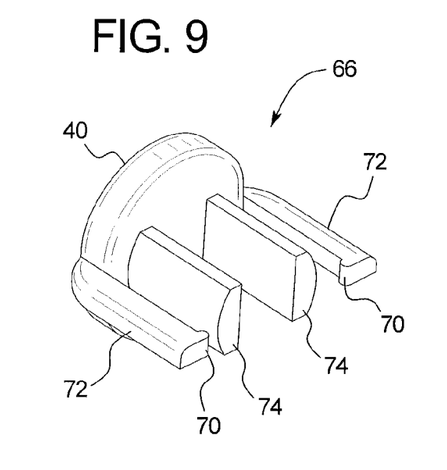
FIG. 9 is a perspective view of an actuator of the suture retention device.

As shown in FIGS. 5-6, the suture retention device 10 may be assembled by sliding the sliding body 16 into the inner cavity 22 of the first housing 12. The spring 18 may then be installed behind the sliding body 16, and the second housing 14 may be attached to the first housing 12 to trap the sliding body 16 and spring 18 within the inner cavity 22. However, it may be preferable to thread the suture 44 through the suture hole 30 before the sliding body 16 is inserted into the inner cavity 22 to make threading the suture 44 easier. The first and second housings 12, 14 may be attached to each other with an adhesive, snap fit, or with threads 86, 88 as shown in FIGS. 7 and 8. The actuator 20 may then be assembled onto the suture retention device 10 by pushing the arms 38 through the openings 36 in the first housing 12, which causes the tabs 54 to flex over the stop surfaces 56. Although the components of the suture retention device 10 may be made in various ways, it may be preferable to form the actuator 20, first housing 12, second housing 14, and sliding body 16 by injection molding using a high density polyethylene. However, due to the flexibility desired for the actuator 20, it may be preferable to form the actuator 20 from low density polyethylene.

Turning the FIGS. 7-12B, another embodiment of the suture retention device 60 is shown. The first housing 62, second housing 64, actuator 66, and sliding body 68 are similar to the components described above, and thus, it is unnecessary to repeat all of the details already described above. One difference with the embodiment of FIGS. 7-12B is that the tabs 70 are located on external arms 72 that extend along the outer surface of the first housing 62. Thus, the internal arms 74 are not provided with tabs and are only used for pressing against the sliding body 68. The first housing 62 is also provided with external flat surfaces 76 for the arms 70 to the slide along and grooves 78 that receive the tabs 70. The stop surface 80 is defined by the end of the grove 78 nearest the openings 82 in the first housing 62. As with the embodiment described above, it is desirable for the removal force to be between about 1 to about 5 N; the durometer of the arms 72 to be between about 30 to about 70 Shore D; and interference between the tabs 70 and the stop surfaces 80 to be about 0.003" to about 0.007". The width of the arms 72 in the direction of flexing is also preferably about 0.035" to about 0.075". Further, it is preferable that the abutment between the sliding body 68 and the inner cavity 22 of the first housing 62 prevents the spring 18 from biasing the tabs 70 against the stop surfaces 80.

Figure 10:
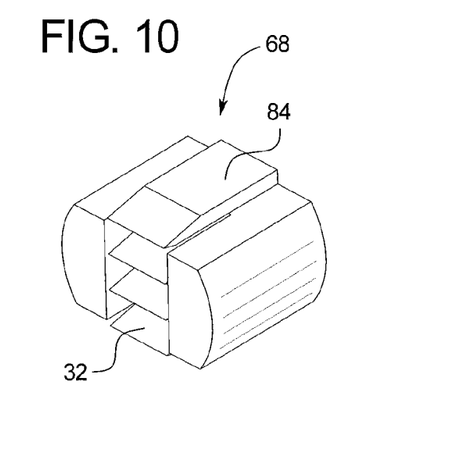
FIG. 10 is a perspective view of a sliding body of the suture retention device.

As shown in FIG. 10, the sliding body 68 may also be provided with a raised rib 84 that slides along a corresponding slot in the first housing 62. The raised rib 84 may be used as a guide surface to control movement between the sliding body 68 and the first housing 62, and may also be used to orient the sliding body 68 to the first housing 62 if the first and second gripping surfaces 28, 32 are provided with asymmetrical surfaces that require the sliding body 68 to be oriented in a particular way. However, the raised rib 84 may also be omitted if so desired.

Figure 11A:
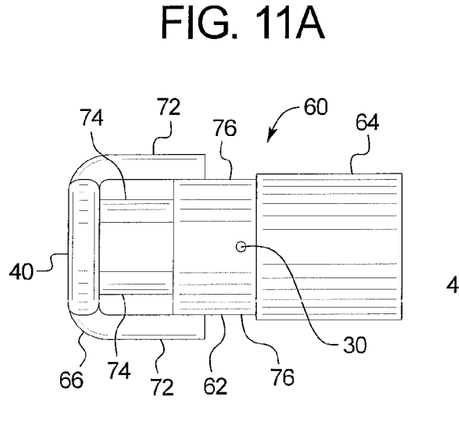
FIG. 11A is a top view of the suture retention member of FIGS. 7-10, showing the suture retention device in a locked state.
Figure 11B:
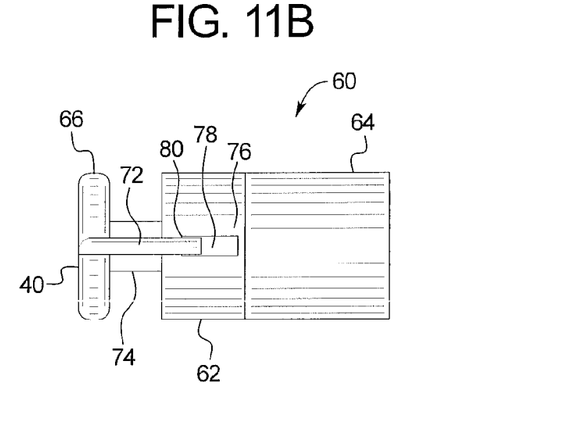
FIG. 11B is a side view of the suture retention device of FIG. 11A.
Figure 12A:
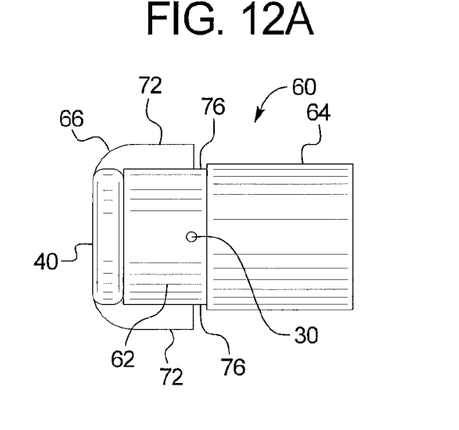
FIG. 12A is a top view of the suture retention member of FIGS. 7-10, showing the suture retention device in an unlocked state.
Figure 12B:
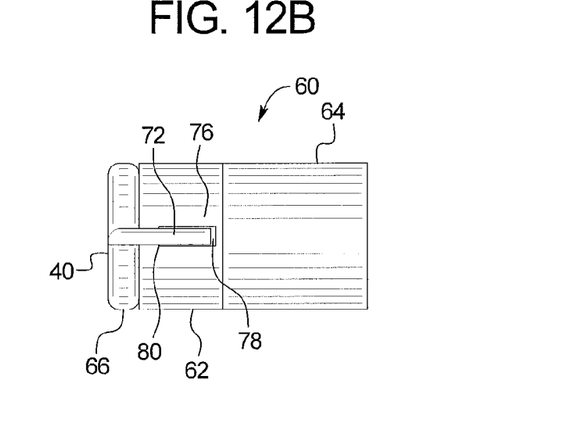
FIG. 12B is a side view of the suture retention device of FIG. 12A.

The locked and unlocked states of the suture retention device 60 are shown FIGS. 11A-12B. FIGS. 11A and 11B show the suture retention device 60 in the locked state, while FIGS. 12A and 12B show the suture retention device 60 in the unlocked state. FIG. 11A shows the locked state from a view facing the suture hole 30. As shown, the internal arms 74 protrude through the openings 82 in the first housing 62 to extend inward toward the inner cavity 22. The external arms 72 extend partially along the flat outer surfaces 76 of the first housing 62. In FIGS. 11A and 12A, the outer surface transition between the first and second housings 62, 64 appears stepped, but preferably this stepped transition only occurs at the flat surfaces 76 around the outer groove 78 in the first housing 62. In contrast, FIGS. 11B and 12B show that the transition between the first and second housings 62, 64 is smooth around the rest of the suture retention device 60. FIG. 11B shows the locked state in a view 90° from the view of FIG. 11A. As shown, the external arms 72 are positioned so that the tabs 70 are adjacent the stop surfaces 80 in the locked state. In FIGS. 12A and 12B, the suture retention device 60 is shown in the unlocked state, which requires a physician to push the actuator 66 to bias the spring 18 and separate the first and second gripping surfaces 28, 32. As shown, the engageable button 40 may abut against the first housing 62 in the unlocked state to indicate that the suture 44 is freely slidable through the suture hole 30. As shown in FIG. 12B, the length of the outer groove 78 is sized to allow the tab 70 to slide within the groove 78 between the locked and unlocked states.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A suture retention device, comprising:
   a housing comprising an inner cavity and a first gripping surface disposed along a first side of said inner cavity;
   a sliding body disposed within said inner cavity and comprising a second gripping surface;
   a spring disposed within said inner cavity and biasing said sliding body toward said first side of said inner cavity to enmesh said first and second gripping surfaces;
   a suture hole extending through said housing and disposed such that a suture extending through said suture hole is enmeshed between said first and second gripping surfaces when said spring biases said sliding body toward said first side of said inner cavity;

an actuator disposed at least partially outside of said housing, said actuator comprising an operator engageable surface outside of said housing, wherein said actuator biases said spring and slides said sliding body away from said first side of said inner cavity to separate said first and second gripping surfaces when an operator engages said engageable surface, a suture thereby be slidable through said suture hole;

wherein said actuator comprises a tab that prevents said actuator from being inadvertently removed from said housing, said tab being flexible so that said actuator is removable from said housing by intentionally pulling said actuator from said housing, said tab engages a stop surface on said housing to prevent inadvertent removal, and said tab is disposed on a second arm extending along an outer surface of said housing and said stop surface is disposed along said outer surface.

2. The suture retention device according to claim 1, wherein said first and second gripping surfaces comprise interlocking teeth.

3. The suture retention device according to claim 1, wherein said housing comprises a first and second housing, said second housing comprising a second side of said inner cavity opposite from said first side.

4. The suture retention device according to claim 1, wherein said housing comprises a first and second housing, said first and second housings being threadably engaged.

5. The suture retention device according to claim 1, wherein said spring is disposed between a second side of said inner cavity opposite from said first side and a rear surface of said sliding body opposite from said second gripping surface.

6. The suture retention device according to claim 1, wherein said actuator comprises a first arm extending through said first side of said inner cavity, said first and second gripping surfaces being separated from each other when an operator pushes said operator engageable surface towards said housing, said first arm thereby pressing said sliding body against said spring.

7. The suture retention device according to claim 1, wherein a force required to remove said actuator is between about 1 to about 5 N.

8. The suture retention device according to claim 1, wherein a durometer of said tab is between about 30 to about 70 Shore D.

9. The suture retention device according to claim 1, wherein an interference between said tab and said stop surface preventing inadvertent removal is about 0.003" to about 0.007".

10. The suture retention device according to claim 1, wherein said spring is restrained due to said sliding body abutting against said inner cavity, said tab thereby not being biased against said stop surface by said spring.

11. The suture retention device according to claim 1, wherein a force required to remove said actuator is between about 1 to about 5 N, a durometer of said tab is between about 30 to about 70 Shore D, and an interference between said tab and said stop surface preventing inadvertent removal is about 0.003" to about 0.007".

12. The suture retention device according to claim 11, wherein said spring is restrained due to said sliding body abutting against said inner cavity, said tab thereby not being biased against said stop surface by said spring.

13. The suture retention device according to claim 12, wherein said spring is disposed between a second side of said inner cavity opposite from said first side and a rear surface of said sliding body opposite from said second gripping surface, and said actuator comprises a first arm extending through said first side of said inner cavity, said first and second gripping surfaces being separated from each other when an operator pushes said operator engageable surface towards said housing, said first arm thereby pressing said sliding body against said spring.

14. The suture retention device according to claim 13, wherein said first and second gripping surfaces comprise interlocking teeth, said housing comprises a first and second housing, said second housing comprising said second side of said inner cavity opposite from said first side, and said first and second housings being threadably engaged.

15. The suture retention device according to claim 1, wherein said first and second gripping surfaces comprise interlocking teeth, said spring is disposed between a second side of said inner cavity opposite from said first side and a rear surface of said sliding body opposite from said second gripping surface, and said actuator comprises a first arm extending through said first side of said inner cavity, said first and second gripping surfaces being separated from each other when an operator pushes said operator engageable surface towards said housing, said first arm thereby pressing said sliding body against said spring.

16. A suture retention device, comprising:
a housing comprising an inner cavity and a first gripping surface disposed along a first side of said inner cavity;
a sliding body disposed within said inner cavity and comprising a second gripping surface;
a spring disposed within said inner cavity and biasing said sliding body toward said first side of said inner cavity to enmesh said first and second gripping surfaces;
a suture hole extending through said housing and disposed such that a suture extending through said suture hole is enmeshed between said first and second gripping surfaces when said spring biases said sliding body toward said first side of said inner cavity;
an actuator disposed at least partially outside of said housing, said actuator comprising an operator engageable surface outside of said housing, wherein said actuator biases said spring and slides said sliding body away from said first side of said inner cavity to separate said first and second gripping surfaces when an operator engages said engageable surface, a suture thereby be slidable through said suture hole;
wherein said actuator comprises a tab that prevents said actuator from being inadvertently removed from said housing, said tab being flexible so that said actuator is removable from said housing by intentionally pulling said actuator from said housing, said tab engages a stop surface on said housing to prevent inadvertent removal, a force required to remove said actuator is between about 1 to about 5 N, a durometer of said tab is between about 30 to about 70 Shore D, and an interference between said tab and said stop surface preventing inadvertent removal is about 0.003" to about 0.007".

17. The suture retention device according to claim 16, wherein said tab is disposed on a first arm extending into said housing and said stop surface is disposed within said housing.

18. The suture retention device according to claim 16, wherein said tab is disposed on a second arm extending along an outer surface of said housing and said stop surface is disposed along said outer surface.

19. The suture retention device according to claim 18, wherein said actuator comprises a first arm extending through said first side of said inner cavity, said first and second gripping surfaces being separated from each other when an operator pushes said operator engageable surface towards said housing, said first arm thereby pressing said sliding body against said spring.

20. The suture retention device according to claim 19, wherein said spring is restrained due to said sliding body abutting against said inner cavity, said tab thereby not being biased against said stop surface by said spring.

\* \* \* \* \*

UNITED STATES PATENT AND TRADEMARK OFFICE
CERTIFICATE OF CORRECTION

| | | |
|---|---|---|
| PATENT NO. | : 9,119,614 B2 | Page 1 of 1 |
| APPLICATION NO. | : 13/766084 | |
| DATED | : September 1, 2015 | |
| INVENTOR(S) | : Kristyn G. Gadlage | |

It is certified that error appears in the above-identified patent and that said Letters Patent is hereby corrected as shown below:

<u>On the Title Page</u>

Items (12) (71) and (72) the Applicant and Inventor last name is spelled wrong, delete "Gadladge" and substitute --Gadlage-- in its place.

Signed and Sealed this
Twenty-ninth Day of December, 2015

Michelle K. Lee
*Director of the United States Patent and Trademark Office*